United States Patent
Jiang et al.

(10) Patent No.: US 12,220,489 B1
(45) Date of Patent: Feb. 11, 2025

(54) MANGANESE-DOPED HOLLOW MESOPOROUS SILICA NANOPARTICLES LOADED WITH CURCUMIN

(71) Applicant: The Affiliated Stomatological Hospital of Nanjing Medical University, Nanjing (CN)

(72) Inventors: Chenghao Jiang, Nanjing (CN); Fei Jiang, Nanjing (CN); Bin Yan, Nanjing (CN); Mingliang Zhou, Shanghai (CN); Yuhan Peng, Nanjing (CN)

(73) Assignee: The Affiliated Stomatological Hospital of Nanjing Medical University, Nanjing (CN)

( * ) Notice: Subject to any disclaimer, the term of this patent is extended or adjusted under 35 U.S.C. 154(b) by 0 days.

(21) Appl. No.: 18/762,795

(22) Filed: Jul. 3, 2024

(30) Foreign Application Priority Data

Aug. 8, 2023 (CN) .......................... 202310988617.8

(51) Int. Cl.
*A61K 9/51* (2006.01)
*A61K 31/12* (2006.01)

(52) U.S. Cl.
CPC .......... *A61K 9/5115* (2013.01); *A61K 9/5123* (2013.01); *A61K 9/5146* (2013.01); *A61K 9/5192* (2013.01); *A61K 31/12* (2013.01)

(58) Field of Classification Search
CPC .................................................. A61K 9/5115
See application file for complete search history.

(56) References Cited

U.S. PATENT DOCUMENTS

2019/0022235 A1* 1/2019 Durfee ................ A61K 47/548

FOREIGN PATENT DOCUMENTS

| CN | 109010850 A | | 12/2018 | |
|---|---|---|---|---|
| CN | 110028072 A | * | 7/2019 | ............. B82Y 40/00 |
| CN | 114394602 A | * | 4/2022 | ............. A61K 49/08 |
| KR | 101631311 B1 | | 6/2016 | |

OTHER PUBLICATIONS

Steven R. Cummings, Arthur C. Santora, Dennis M. Black, R. Graham G. Russell. "History of alendronate." Bone, vol. 137, 2020, 115411, pp. 1-7. (Year: 2020).*

Julie Bolley et al. "Carbodiimide versus Click Chemistry for Nanoparticle Surface Functionalization: A Comparative Study for the Elaboration of Multimodal Superparamagnetic Nanoparticles Targeting αvβ3 Integrins." Langmuir, vol. 29, 2013, pp. 14639-14647. (Year: 2013).*

(Continued)

*Primary Examiner* — Isaac Shomer
(74) *Attorney, Agent, or Firm* — Pilloff Passino & Cosenza LLP; Rachel Pilloff; Sean Passino

(57) ABSTRACT

Manganese-doped hollow mesoporous silica nanoparticles loaded with curcumin and an application in periodontal bone tissue repair are provided in the present disclosure, belonging to the technical field of targeted delivery of nanoparticles and bone tissue regeneration. In the present disclosure, alendronate is grafted on the surface of silica nanoparticles to achieve bone targeting, manganese is doped on the nanoparticles by a chemical method, and curcumin is wrapped in the nanoparticles.

7 Claims, 29 Drawing Sheets

(56) References Cited

OTHER PUBLICATIONS

Deng et al. "A Hollow Mesoporous Silicon Dioxide Nano-material Doped With Manganese and Preparation Method and Application Thereof." English Translation of CN 114394602 A, obtained by examiner on Aug. 19, 2024, originally published in Chinese on Apr. 26, 2022, pp. 1-8. (Year: 2022).*

Sumedh Kamble, Pegah Varamini, Markus Mullner, Theophile Pelras and Ramin Rohanizadeh. "Bisphosphonate-functionalized micelles for targeted delivery of curcumin to metastatic bone cancer." Pharmaceutical Development and Technology, vol. 25, No. 9, 2020, pp. 1118-1126. (Year: 2020).*

Fei et al. "A Manganese-doped Mesoporous Silicon Dioxide Nano-particle Preparation Method." English Translation of CN 110028072 A. Obtained by examiner on Aug. 19, 2024, originally published in Chinese on Jul. 19, 2019, pp. 1-6. (Year: 2019).*

Yu Luodan et al, ""Manganese Extraction" Strategy Enables Tumor-Sensitive Biodegradability and Theranostics of Nanoparticles," Journal of the American Chemical Society, Date of issue: Jul. 21, 2016, pp. 9881-9894, vol. 138. Related claims: 1-10.

Zhang Yu, "Preparation of functional element-doped mesoporous silica/composite and its application in tissue damage repair," "China Doctoral Dissertation Full-text Database Engineering Technology Series 1", No. 05. Date of issue: May 15, 2020, p. 19-20, B015-5: p. I-I-I II, Related claims: 1-10.

Wei Liping et al., "Effects of curcumin on the activity of Mn-infected BV2 cells and inflammatory factor TNF-α," Journal of Southern Xiangnan University (Medical Edition), Date of issue: Mar. 31, 2022, p. 12-17, vol. 24, No. 1. Related claims: 1-10.

First Office Action for China Application No. 202310988617.8, mailed Mar. 13, 2024.

Notification to Grant Patent for China Application No. 202310988617.8, mailed Mar. 29, 2024.

First Search Report for China Application No. 202310988617.8, dated Mar. 11, 2024.

Supplementary Search Report for China Application No. 202310988617.8, dated Mar. 11, 2024.

* cited by examiner

MANGANESE-DOPED HOLLOW MESOPOROUS SILICA NANOPARTICLES LOADED WITH CURCUMIN

CROSS-REFERENCE TO RELATED APPLICATIONS

This application claims priority to Chinese Patent Application No. 202310988617.8, filed on Aug. 8, 2023, the contents of which are hereby incorporated by reference.

TECHNICAL FIELD

The present disclosure belongs to the technical field of targeted delivery of nanoparticles and bone tissue regeneration, and in particular to manganese-doped hollow mesoporous silica nanoparticles loaded with curcumin and an application thereof in periodontal bone tissue repair.

BACKGROUND

As a serious oral disease, periodontitis is the leading cause of tooth loss in adults and is mainly characterized by loss of attachment of the gums and resorption of the alveolar bone. Loss of periodontal bone support leads to decreased chewing function and loosening of teeth, severely affecting the quality of life of patients. Nowadays, studies show that the causes of periodontitis are related to the bacteria in the cervical biofilm of the tooth and their virulence factors (lipopolysaccharide) that stimulate a series of immune responses in the host, and the alteration of the microenvironment of periodontitis promotes the polarisation of macrophages in the direction of M1, and the enhancement of inflammatory factor secretion, suppressing osteogenesis and promoting osteoblastogenesis, making it crucial to improve the microenvironment and suppressing the growth of periodontal bacteria in a long term manner.

Existing treatment modalities for periodontitis bone defects include basic periodontal treatment (supragingival scaling, subgingival scraping with root planing), periodontal adjuvant treatment (systemic antibiotics, local medications), and periodontal surgical treatment (guided tissue regeneration (GTR), guided bone regeneration (GBR), flap surgery). With the continuous development and maturation of nano-technology, nanoparticle-based release and control systems have shown good therapeutic effects in periodontitis bone defects. Although there are reports related to the application of nanoparticles to periodontal bone tissue repair, there is a lack of bone targeting, with no report on metal-natural polyphenol synergistic antimicrobial and anti-inflammatory osteogenesis system; and due to the special anatomical structure of periodontal bone tissues, the operation space is limited, and the local release of the drug concentration in the periodontal bone tissues is too fast, with the requirement of long-lasting maintenance of the drug concentration not being achieved; therefore, the present disclosure proposes a kind of manganese-doped hollow mesoporous silica nanoparticles loaded with curcumin, which are applied in the periodontal bone tissue repair.

SUMMARY

In order to solve the above technical problems, the present disclosure provides manganese-doped hollow mesoporous silica nanoparticles loaded with curcumin and an application thereof in periodontal bone tissue repair.

In order to achieve the above objectives, the present disclosure provides the following technical scheme.

The present disclosure provides a preparation method of manganese-doped hollow mesoporous silica nanoparticles loaded with curcumin, including the following steps:

mixing silica nanoparticles ($SiO_2$ nanoparticles) with ethanol, ammonia (with a volume fraction of 28%-30%), and cetyltrimethyl ammonium bromide (CTAB) to obtain a mixture aqueous solution, followed by dropwise adding 3-aminopropyltriethoxysilane (APTES) to the mixture aqueous solution, and stirring and reacting for 2 hours (h) at room temperature, then continuing stirring for 24 h at 50 degrees Celsius (° C.), followed by centrifugation (14,000 revolutions per minute (rpm) for 5 min) to obtain mesoporous silica particles with a shell-core structure;

mixing the mesoporous silica particles with the shell-core structure with a sodium carbonate solution for reaction, washing with ethanol for three times, and vacuum drying to obtain aminated silica particles with hollow structure;

mixing and stirring the aminated silica particles with hollow structure with manganese chloride, dropwise adding ammonia water (30 wt %), transferring into a reaction kettle, heating at 140° C. for 10 h, centrifugally washing a product (18,000 rpm, 15 min) to remove residues, adding the product into a mixed solution of hydrochloric acid and ethanol, reacting at 60° C. for 12 h to extract a surfactant, and washing to obtain manganese-doped hollow mesoporous silica nanoparticles;

dispersing the manganese-doped hollow mesoporous silica nanoparticles (Mn-HMSN) in borate buffer salt solution (BBS, pH=7.4-9.2, 0.2 molarity (M)) for solution replacement, then adding active ester-polyethylene glycol-carboxyl group (NHS-PEG-COOH) for overnight reaction to obtain PEG-modified Mn-HMSN, followed by ultrafiltration with an ultrafiltration tube to remove unreacted PEG material;

dispersing the PEG-modified Mn-HMSN with BBS buffer solution (pH=7.4-9.2, 0.2 M), adding ethyl dimethylaminopropyl carbodiimide (EDC·HCl) and N-hydroxysuccinimide (NHS) for reaction, then adding alendronate for reaction, followed by ultrafiltration, concentration and solution displacement, to obtain the bisphosphonate-modified nanoparticles (BP/Mn-HMSN); and adding the bisphosphonate-modified nanoparticles (BP/Mn-HMSN) into a curcumin solution (obtained by mixing curcumin and ethanol according to a material-liquid ratio of 10 milligrams (mg):5 milliliters (mL)) for reaction, centrifuging at 12,000 rpm for 5 min, and rinsing with ethanol twice to obtain the manganese-doped hollow mesoporous silica nanoparticles (Cur@Mn-HMSN) loaded with curcumin, and suspending in sterile water for later use.

Optionally, a preparation method of the silica nanoparticles ($SiO_2$ nanoparticles) includes the following steps: mixing ethanol, water and ammonia water according to a volume ratio of 30:3:1, stirring (500 rpm) at room temperature, then adding tetraethyl orthosilicate (TEOS, from Sinopharm Chemical Reagent Co., Ltd.), continuing to react at 30° C. for 1 h, centrifugally collecting the product, washing with ethanol and water for three times, and vacuum drying at room temperature to obtain the silica nanoparticles ($SiO_2$ nanoparticles).

Optionally, a material-liquid ratio of the silica nanoparticles to 3-aminopropyltriethoxysilane and cetyltrimethyl ammonium bromide is 10-50 mg:20 μL:11.2 mg. More optionally, the material-liquid ratio of the silica nanoparticles to 3-aminopropyltriethoxysilane and cetyltrimethyl ammonium bromide is 20 mg:20 μL:11.2 mg.

Optionally, a concentration of the sodium carbonate solution is 1 M, and an addition of the sodium carbonate solution is followed by stirring and reacting at 45° C. for 6 h.

Optionally, a dosage ratio of the manganese-doped hollow mesoporous silica nanoparticles to the active ester-polyethylene glycol-carboxyl group is 10-50 mg:100 mg. Preferably, the dosage ratio of the manganese-doped hollow mesoporous silica nanoparticles to the active ester-polyethylene glycol-carboxyl group is 20 mg:100 mg.

Optionally, a dosage ratio of the aminated silica particles with hollow structure to the manganese chloride is 10-50 mg:20 mg. Preferably, the dosage ratio of the aminated silica particles with hollow structure to the manganese chloride is 10 mg:20 mg.

Optionally, a dosage ratio of the PEG-modified manganese-doped silica particles to the ethyl dimethylaminopropyl carbodiimide, N-hydroxysuccinimide and alendronate is 10-50 mg:12 mg:8 mg:8 mg, and the alendronate is added to react overnight at room temperature. Preferably, the dosage ratio of the PEG-modified manganese-doped silica particles to the ethyl dimethylaminopropyl carbodiimide, N-hydroxysuccinimide and alendronate is 20 mg:12 mg:8 mg:8 mg.

Optionally, a mass ratio of the bisphosphonate-modified silica particles to curcumin in the curcumin solution is 1:1, and the bisphosphonate-modified silica particles are added into curcumin solution and reacted by shaking overnight away from light.

The present disclosure also provides manganese-doped hollow mesoporous silica nanoparticles loaded with curcumin, which is prepared by the preparation method above.

The present disclosure also provides an application of the manganese-doped hollow mesoporous silica nanoparticles loaded with curcumin in periodontal bone tissue repair.

Optionally, a concentration of the manganese-doped hollow mesoporous silica nanoparticles loaded with curcumin is 2.5 micrograms per milliliter (μg/mL).

Compared with the prior art, the present disclosure has the following advantages and technical effects.

The manganese-doped hollow mesoporous silica nanoparticles loaded with curcumin prepared by the present disclosure achieve bone targeting by grafting alendronate on the surface of the nanoparticles.

The manganese-doped hollow mesoporous silica nanoparticles loaded with curcumin prepared by the present disclosure take Mn ions and curcumin as the treatment system for the first time, and the system has the synergistic therapeutic effects of anti-inflammatory, antibacterial and osteogenesis promotion.

The manganese-doped hollow mesoporous silica nanoparticles loaded with curcumin prepared by the present disclosure have good antibacterial, anti-inflammatory and osteogenic differentiation promoting functions.

The manganese-doped hollow mesoporous silica nanoparticles loaded with curcumin prepared by the present disclosure have the function of promoting the repair of mouse periodontal bone tissue.

In the whole preparation process of the manganese-doped hollow mesoporous silica nanoparticles loaded with curcumin, special, complicated and expensive equipment is not required, and the operation process is simple, which is beneficial to popularization and application.

BRIEF DESCRIPTION OF THE DRAWINGS

The accompanying drawings, which constitute a part of this application, are used to provide a further understanding of this application. The illustrative embodiments of this application and their descriptions are used to explain this application, and do not constitute an improper limitation of this application. In the attached images.

DETAILED DESCRIPTION OF THE EMBODIMENTS

Figure 1:
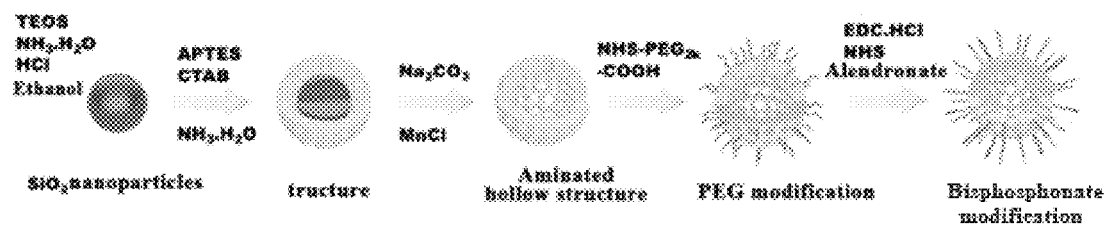
FIG. 1 illustrates a process of preparing bisphosphonate-modified silica particles (BP/Mn-HMSN) from $SiO_2$ nanoparticles in Embodiment 1.

A number of exemplary embodiments of the present disclosure are now described in detail, and this detailed description should not be considered as a limitation of the present disclosure, but should be understood as a more detailed description of certain aspects, characteristics and embodiments of the present disclosure.

It should be understood that the terminology described in the present disclosure is only for describing specific embodiments and is not used to limit the present disclosure. In addition, for the numerical range in the present disclosure, it should be understood that each intermediate value between the upper limit and the lower limit of the range is also specifically disclosed. The intermediate value within any stated value or stated range and every smaller range between any other stated value or intermediate value within the stated range are also included in the present disclosure. The upper and lower limits of these smaller ranges can be independently included or excluded from the range.

Unless otherwise specified, all technical and scientific terms used herein have the same meaning as commonly understood by one of ordinary skill in the art to which this present disclosure relates. Although the present disclosure only describes the preferred methods and materials, any methods and materials similar or equivalent to those described herein may also be used in the practice or testing of the present disclosure. All documents mentioned in this specification are incorporated by reference to disclose and describe methods and/or materials related to the documents. In case of conflict with any incorporated document, the contents of this specification shall prevail.

It is obvious to those skilled in the art that many improvements and changes may be made to the specific embodiments of the present disclosure without departing from the scope or spirit of the present disclosure. Other embodiments will be apparent to the skilled person from the description of the present disclosure. The description and embodiments of that present disclosure are exemplary only.

The terms "including", "comprising", "having" and "containing" used in this specification are all open terms, which means including but not limited to.

All the raw materials used in the embodiments of the present disclosure are obtained by commercial purchase.

The room temperature in the embodiments of the present disclosure refers to 25+/−2° C.

The technical schemes of the present disclosure will be further explained by embodiments.

Embodiment 1

Ethanol, water and ammonia water are mixed according to the volume ratio of 30:3:1, stirred at room temperature (500 rpm), then 1.5 mL of TEOS (Sinopharm Chemical Reagent Co., Ltd.) is added, and the reaction is continued at 30° C. for 1 h. After the product is collected by centrifugation (12,000 rpm, 10 min), the product is washed with ethanol and water for three times, and vacuum dried at room temperature to obtain $SiO_2$ nanoparticles.

20 mg $SiO_2$ nanoparticles are mixed with 20 mL of ethanol, 624 µL of ammonia water (28%-30% by volume fraction) and 11.2 mg of cetyltrimethyl ammonium bromide (CTAB) to obtain a mixture aqueous solution, then 20 µL of 3-aminopropyltriethoxysilane (APTES) is added dropwise to the mixture aqueous solution, stirred at room temperature for 2 h, then stirred for 24 h at 50° C., then centrifugation (14,000 rpm, 5 min) is performed to obtain mesoporous silica particles with shell-core structure.

20 mg of the mesoporous silica particles with shell-core structure and 20 mL of sodium carbonate solution (concentration of 1 M) are mixed and stirred at 45° C. for 6 h, and the product is washed with ethanol for three times and dried in vacuum to obtain aminated silica particles with hollow structure.

10 mg of aminated silica particles with hollow structure and 20 mg of manganese chloride are mixed and stirred for 20 min, then ammonia water (30 wt %, 0.6 mL) is added dropwise, and the mixture is heated at 140° C. for 10 h, and the product is centrifugally washed (18,000 rpm, 15 min) to remove the residue, and it is added to the mixed solution of hydrochloric acid and ethanol (the volume ratio of hydrochloric acid to ethanol is 1:10), followed by reaction at 60° C. for 12 h to remove the residual CTAB and washing to obtain the manganese-doped hollow mesoporous silica nanoparticles.

20 mg of the manganese-doped hollow mesoporous silica nanoparticles is dispersed in 20 mL of borate buffer salt solution (BBS buffer solution, pH=7.4-9.2, 0.2 M) for solution replacement, and then 100 mg of active ester-polyethylene glycol-carboxyl group (NHS-PEG2k-COOH) is added to react for 5 h to obtain PEG-modified manganese-doped silica particles (Mn-HMSN), and the unreacted PEG polymer molecules are removed by dialysis using ultrafiltration tube (molecular weight cut-off 100 kilodaltons (KDa)).

20 mg of PEG-modified manganese-doped silica particles are dispersed in 20 mL of borate buffer salt solution (BBS buffer solution, pH=7.4-9.2, 0.2 M), 12 mg of ethyl dimethylaminopropyl carbodiimide (EDC·HCl) and 8 mg of N-hydroxysuccinimide (NHS) are added to react at room temperature for 0.5 h, and then concentrated by ultrafiltration (molecular weight cut-off is 100 KDa), followed by re-dispersing in borate buffer salt solution (BBS buffer solution, pH=7.4-9.2, 0.2 M), then 8 mg alendronate is added to react overnight at room temperature, followed by ultrafiltration, concentration and solution replacement to obtain bisphosphonate-modified silica particles (BP/Mn-HMSN).

10 mg of bisphosphonate-modified silica particles (Mn-HMSN) is added into curcumin solution obtained by dissolving 10 mg of curcumin in 5 mL of ethanol, followed by shaking in a shaking table overnight in the dark, then the product is centrifuged at 12,000 rpm for 5 min, and rinsed with ethanol twice to obtain manganese-doped hollow mesoporous silica nanoparticles (Cur@Mn-HMSN) loaded with curcumin.

The process of preparing bisphosphonate-modified silica particles (BP/Mn-HMSN) from $SiO_2$ nanoparticles is shown in FIG. 1.

Performance Tests

I. Detection of Drug Entrapment Efficiency

The UV absorption standard curves of curcumin with different concentrations in ethanol are drawn according to equal dilution, and the curcumin content in the manganese-doped hollow mesoporous silica nanoparticles loaded with curcumin (Cur@Mn-HMSN) prepared in Embodiment 1 is calculated, where the drug entrapment efficiency=(initial curcumin mass-curcumin mass in solution)/initial curcumin mass, and the entrapment efficiency of curcumin in Cur@Mn-HMSN obtained in Embodiment 1 is 90%.

II. Transmission Electron Microscope and Mapping Analysis

Figure 2:
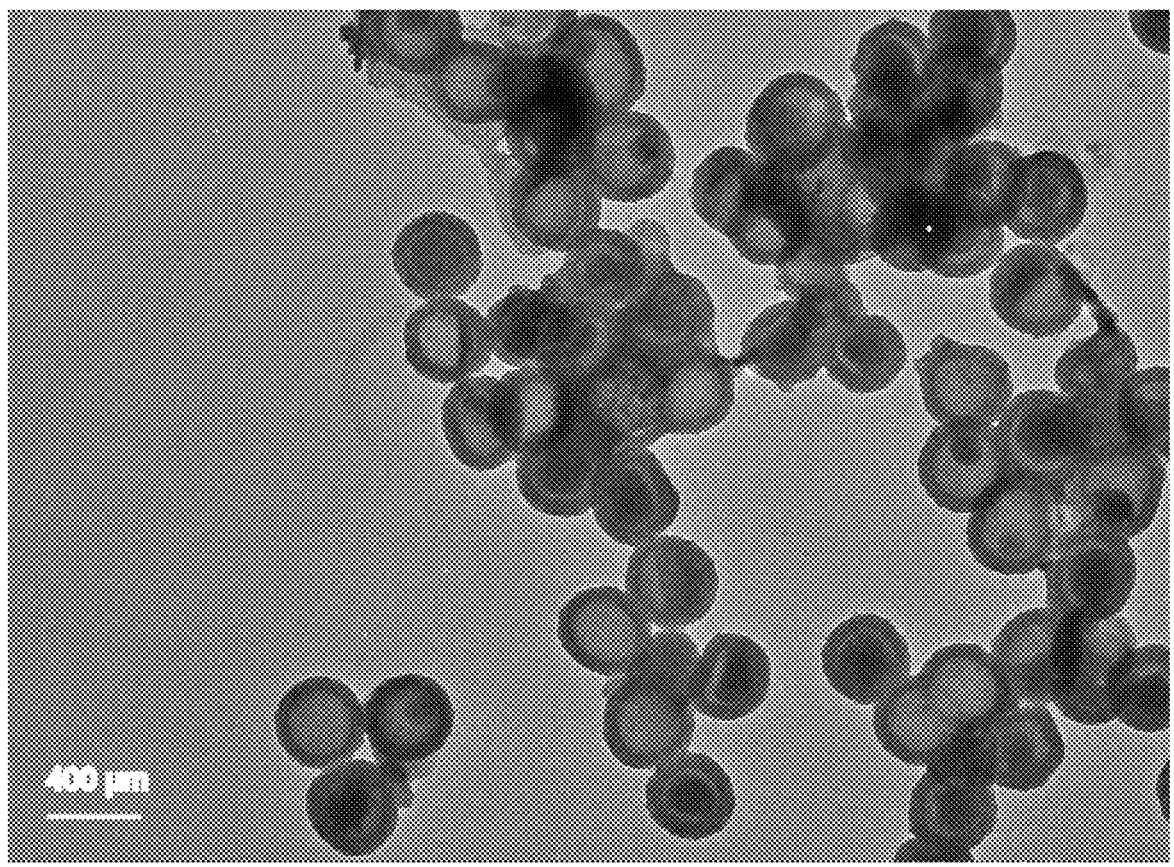
FIG. 2 is a transmission electron microscope (TEM) image (×10,000 times) of manganese-doped hollow mesoporous silica nanoparticles (Cur@Mn-HMSN) loaded with curcumin prepared in Embodiment 1.
Figure 3A:
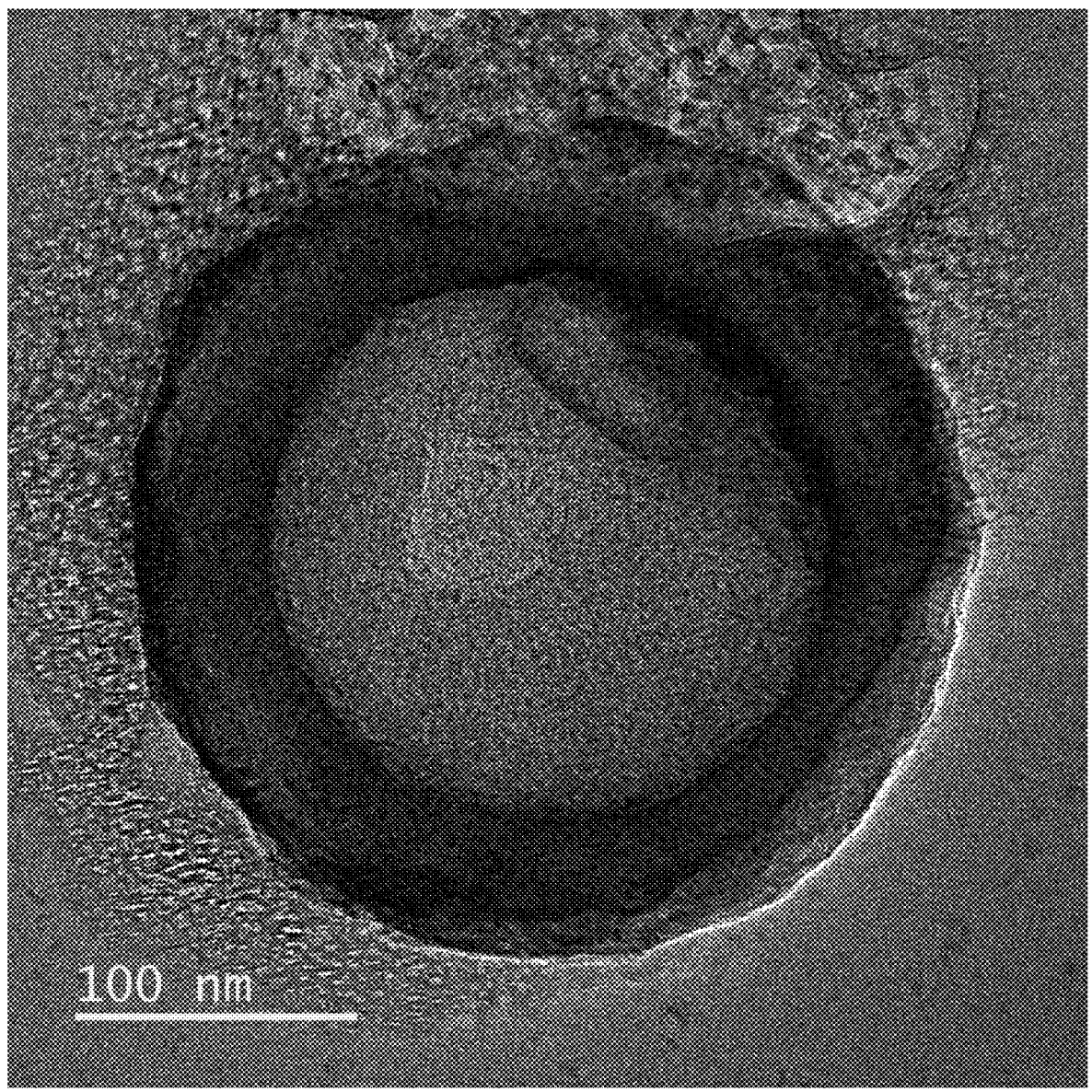
FIG. 3A is a TEM image result (×500,000 times) of manganese-doped hollow mesoporous silica nanoparticles (Cur@Mn-HMSN) loaded with curcumin prepared in Embodiment 1.
Figure 3B:
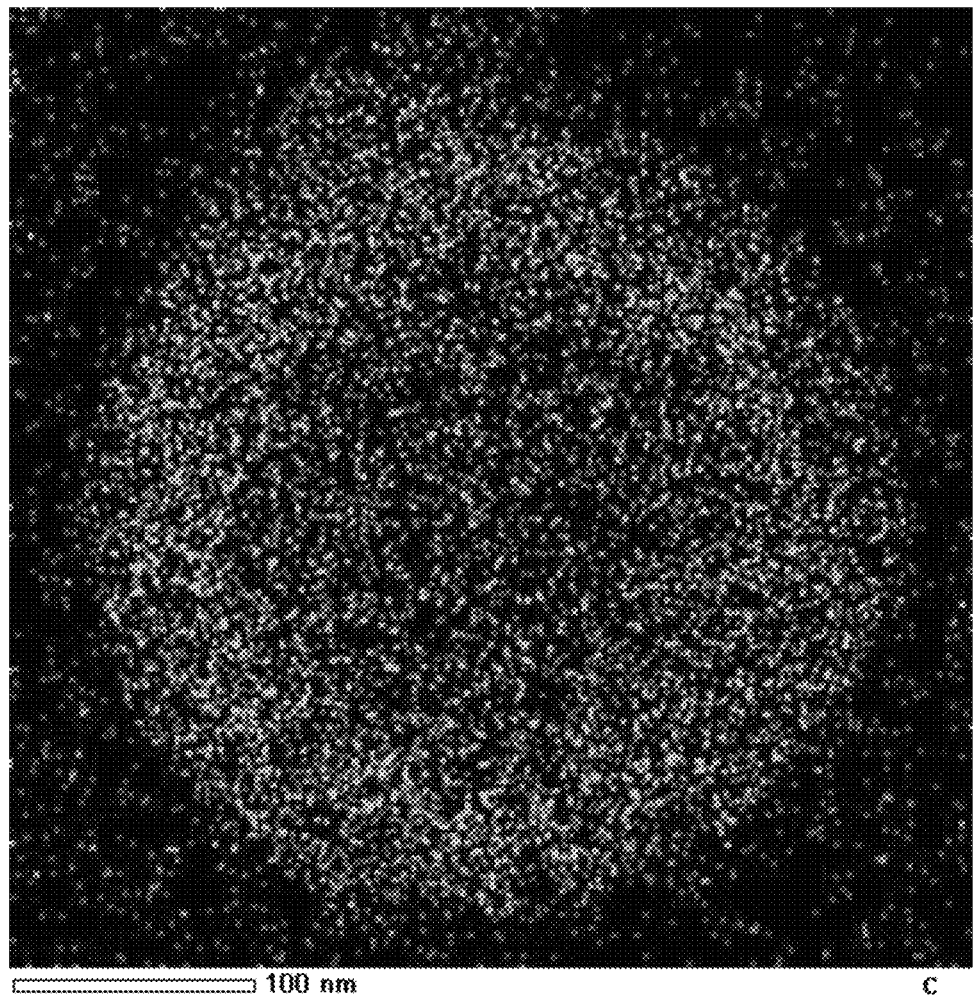
FIG. 3B shows the Mapping analysis result of C.
Figure 3C:
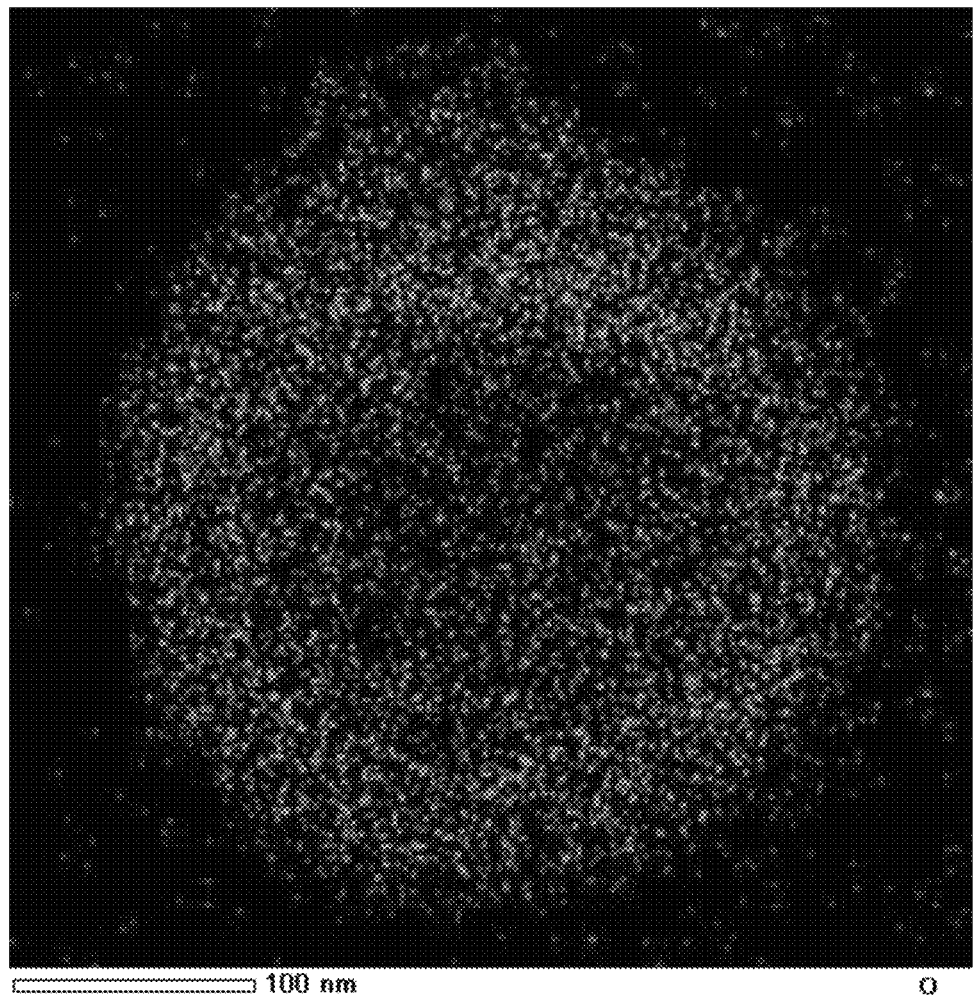
FIG. 3C is the Mapping analysis result of O.
Figure 3D:
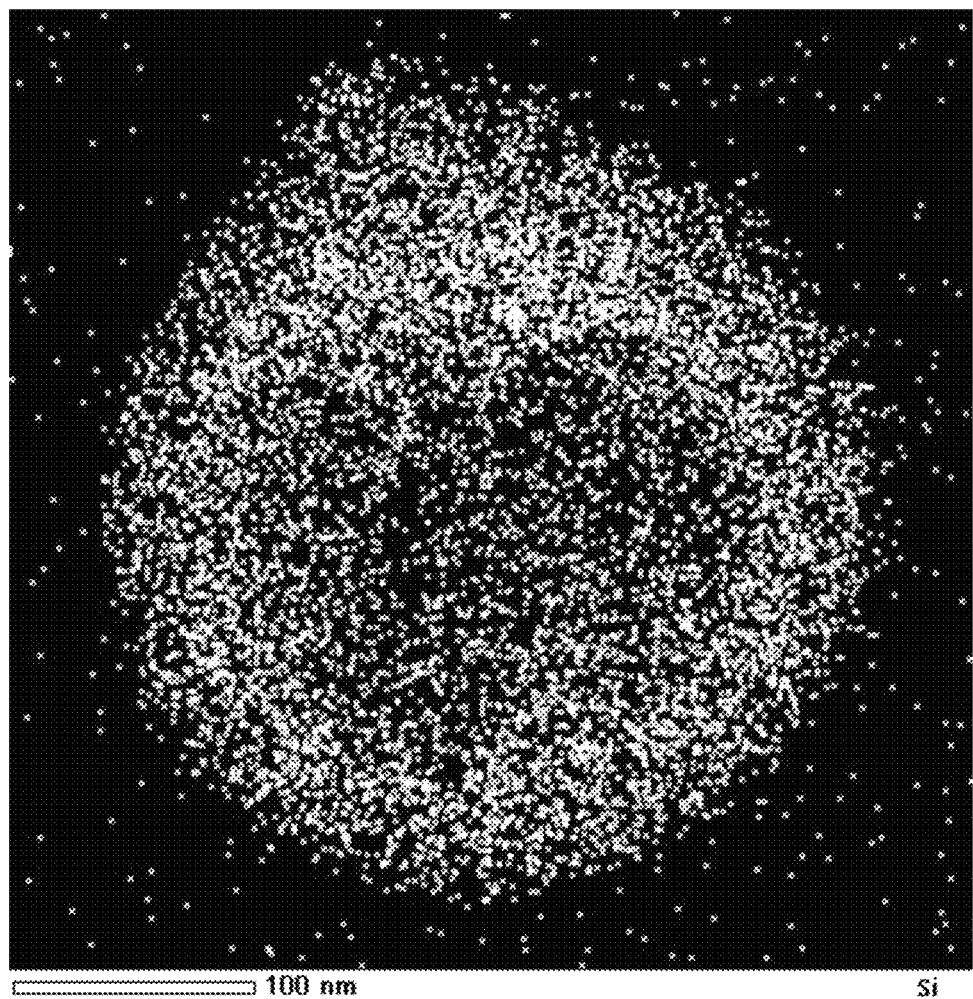
FIG. 3D is the Mapping analysis result of Si.
Figure 3E:
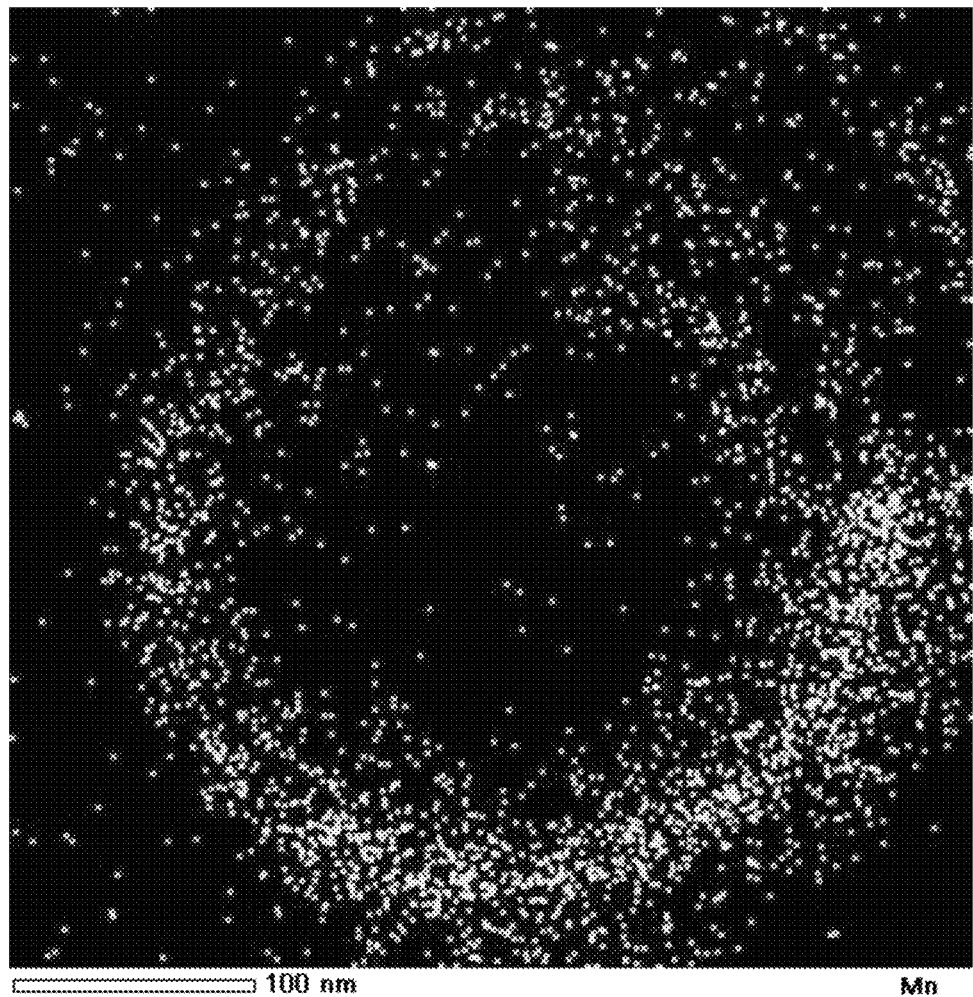
FIG. 3E is the Mapping analysis result of Mn.
Figure 3F:
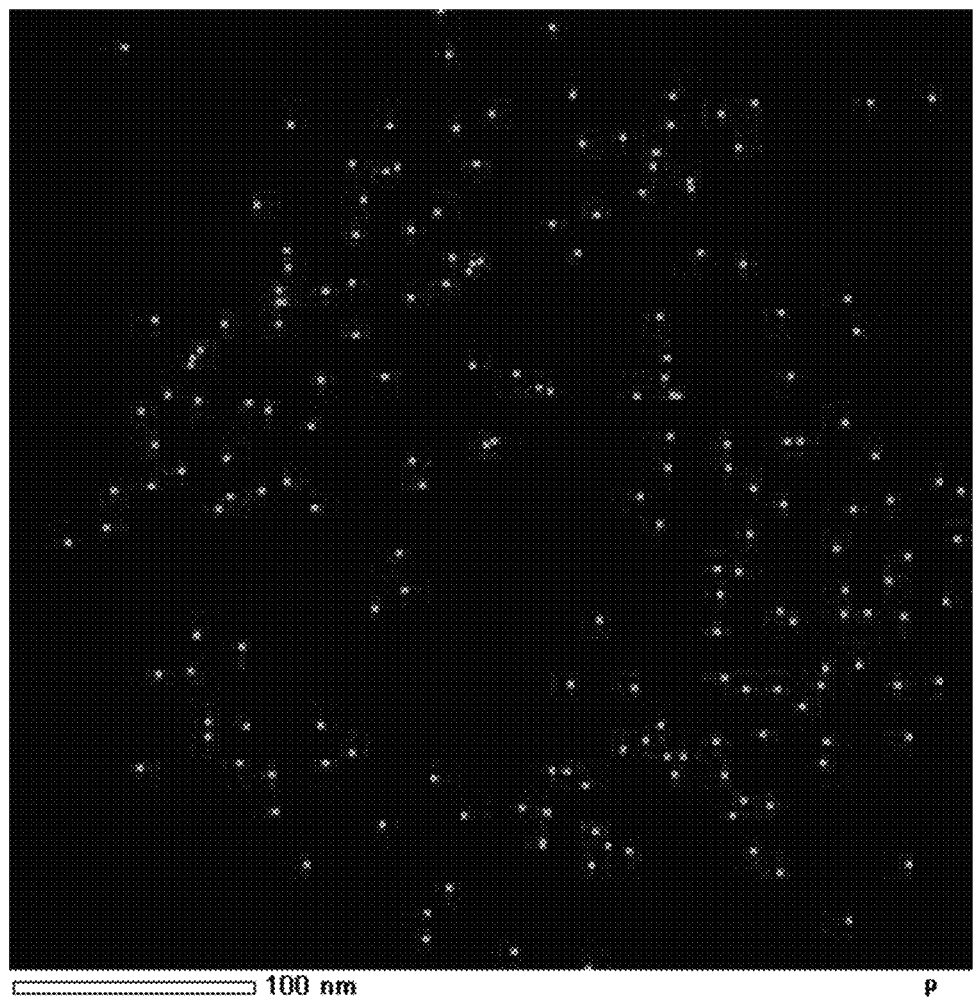
FIG. 3F is the Mapping analysis result of P.

The transmission electron microscope image (×10,000 times) of manganese-doped hollow mesoporous silica nanoparticles loaded with curcumin (Cur@Mn-HMSN) prepared in Embodiment 1 is shown in FIG. 2, and the transmission electron microscope results and Mapping analysis results at ×500,000 times are shown in FIG. 3A-FIG. 3F, where FIG. 3A is the transmission electron microscope result (×500,000 times), FIG. 3B is the Mapping analysis result of C, and FIG. 3C is the Mapping analysis result of O, FIG. 3D is the Mapping analysis result of Si, FIG. 3E is the Mapping analysis result of Mn, and FIG. 3F is the Mapping analysis result of P. As may be seen from FIG. 2 and FIG. 3A-FIG. 3F, Mn ions, P ions and other related ions are expressed, which proves that bisphosphonates are grafted on nanoparticles.

III. Bone Targeting Test

Figure 4:
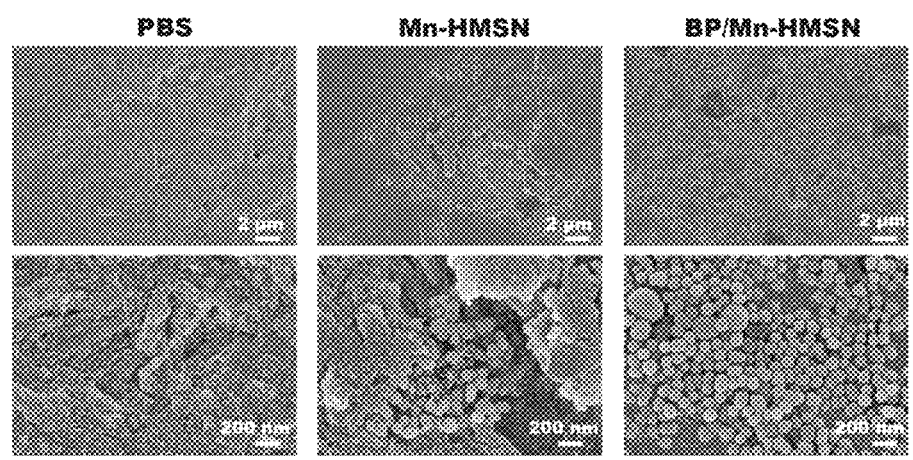
FIG. 4 shows the scanning electron micrographs of the Mn-HMSN, BP/Mn-HMSN and PBS groups in the bone targeting test, with the top row being the scanning electron micrographs at 2 μm and the bottom row being the scanning electron micrographs at 200 nm.

The PEG-modified manganese-doped silica particles (Mn-HMSN) and bisphosphonate-modified silica particles (BP/Mn-HMSN) prepared in Embodiment 1 are respectively dispersed in PBS at a rate of 0.5 mg/mL, and the bovine cortical bone fragments are soaked in them and left at 37° C. for 24 h. Subsequently, the bone fragments are transferred to deionized water, and rinsed slowly for 10 min at room temperature for three times. Finally, the bone fragments are oven-dried and the surface microstructural changes are observed by electron microscopy using field emission scanning electron microscopy (FE-SEM, Hitachi, Japan) with only PBS added as a control. The scanning electron micrographs are shown in FIG. 4, with the top row being at 2 μm and the bottom row being at 200 nm. As shown in FIG. 4, the modified nanoparticles may be bound to the surface of bone fragments with bone targeting.

IV. Selection of Therapeutic Concentration

The manganese-doped hollow mesoporous silica nanoparticles loaded with curcumin (Cur@Mn-HMSN) prepared in Embodiment 1 are added to DMEM substrate containing 10% fetal bovine serum, so that their concentrations are 0 μg/mL, 2.5 μg/mL, 5 μg/mL and 10 μg/mL in turn. The PEG-modified manganese-doped silica particles (Mn-HMSN) prepared in Embodiment 1 are treated in the same way.

Figure 5A:
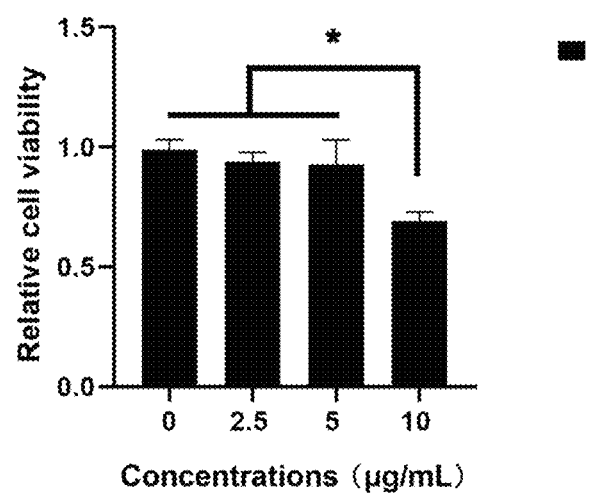
FIG. 5A shows the results of relative cell proliferation rates of periodontal ligament stem cells at different concentrations of Mn-HMSN.
Figure 5B:
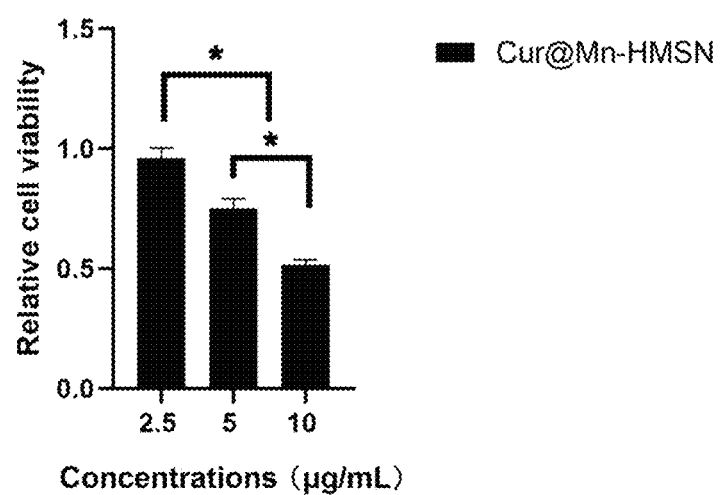
FIG. 5B shows the results of relative cell proliferation rates of periodontal ligament stem cells at different concentrations of Cur@Mn-HMSN.

Human periodontal ligament stem cells (hPDLSCs, isolated and preserved as in Proc Natl Acad Sci U.S.A. 2000, 5; 97 (25):13625-30), that is, the hPDLSCs are inoculated in a 96-well plate at a density of 3,000 cells/well, and after overnight waiting for the cells to attach to the wall and then replacing with the previously prepared substrate respectively to continue the culture, the substrate is aspirated after 48 h, and washed by PBS for 2 times, then a fresh substrate containing CCK-8 reagent is added to continue the incubation for 1 h. Absorbance at 450 nm is detected, and the relative proliferation rate of the cells is calculated, with results shown in FIG. 5, from which it is observed that the optimal concentration of manganese-doped hollow mesoporous silica nanoparticles loaded with curcumin (Cur@Mn-HMSN) in periodontal bone tissue repair is 2.5 μg/mL.

Figure 6:
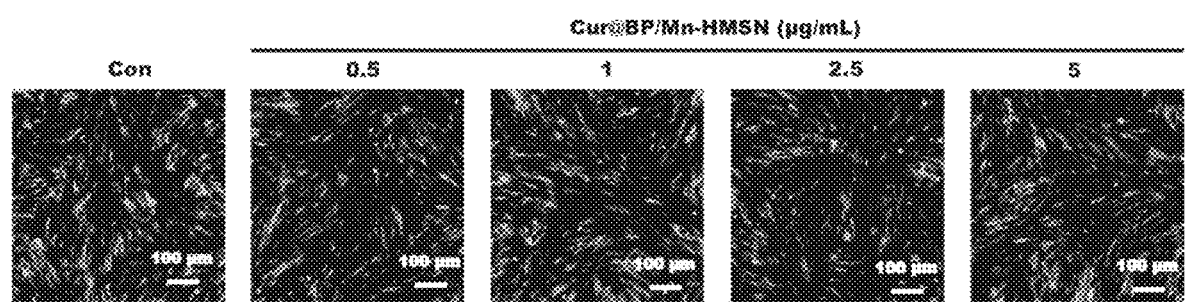
FIG. 6 shows SEM images of cells after live-dead staining with different Cur@Mn-HMSN concentrations of substrate and Con groups.

Human periodontal ligament stem cells (hPDLSCs) are inoculated into a 6-well plate and cultured overnight. After the cells are attached to the wall, the substrate with different Cur@Mn-HMSN concentrations as mentioned above are used for replacement to continue the culture, and the substrate without Cur@Mn-HMSN is used as a control (Con). 24 hours later, the substrates are aspirated, washed twice with PBS, and the cells are added with cell live-dead staining solution for the live-dead staining (The live-dead staining detection reagent is purchased from Yeasen Biotechnology), incubated at 37° C. for 15-30 min, and observed under an inverted microscope, the SEM image after staining is shown in FIG. 6, which shows that the cytotoxicity of nanoparticles on periodontal ligament stem cells is dose-dependent.

V. Osteogenesis Induction Experiment

Figure 7:
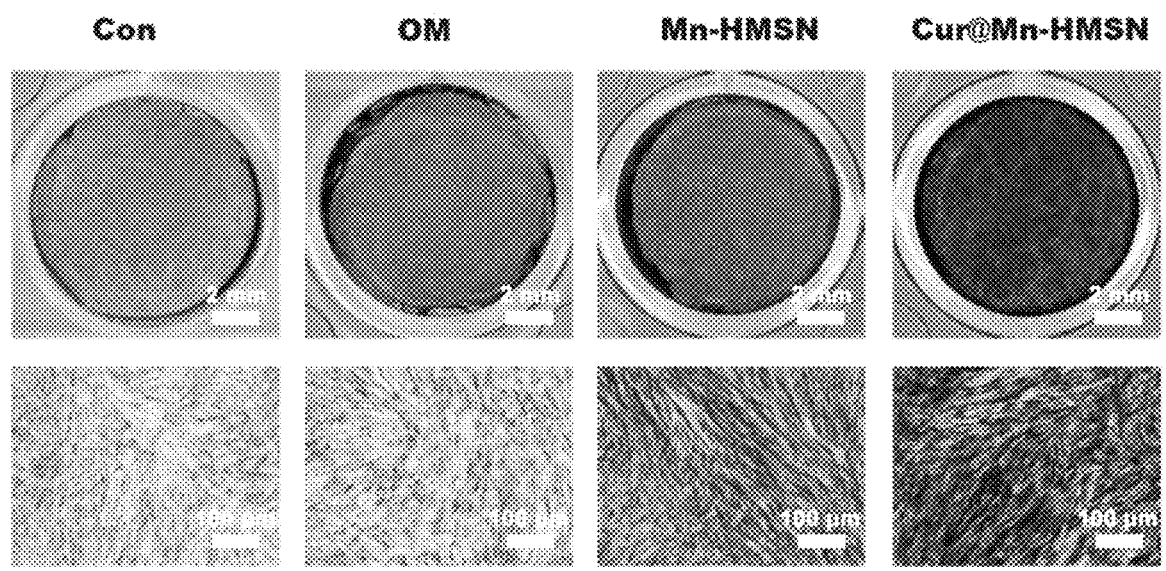
FIG. 7 shows the results before and after dyeing with alkaline phosphatase staining reagent in Cur@Mn-HMSN group, Mn-HMSN group, Con group and OM group in osteogenesis induction experiment.
Figure 8:
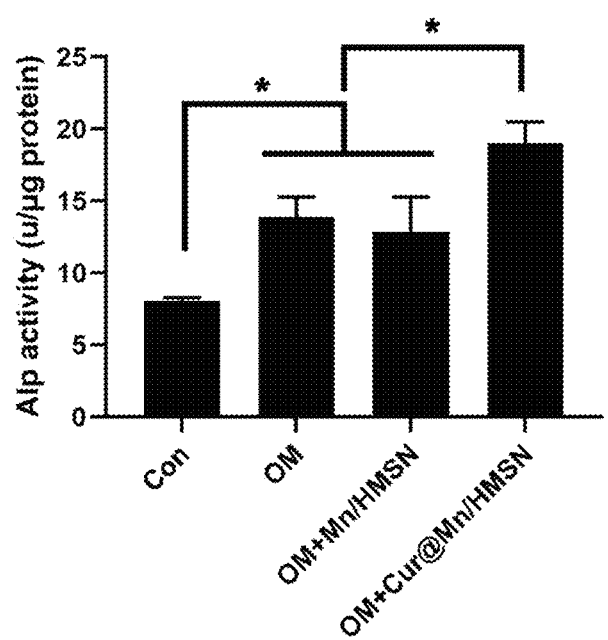
FIG. 8 shows the expression level structures of intracellular alkaline phosphatase in Cur@Mn-HMSN group, Mn-HMSN group, Con group and OM group in osteogenesis induction experiment.
Figure 9A:
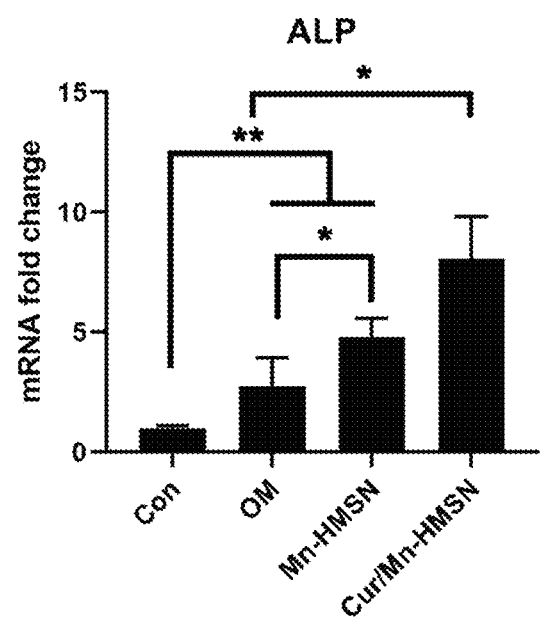
FIG. 9A shows the measurement results of intracellular ALP in Cur@Mn-HMSN group, Mn-HMSN group, Con group and OM group in the osteogenesis induction experiment, in which gray represents Con group, red represents OM group, blue represents Mn-HMSN group and green represents CUR @ Mn-HMSN.
Figure 9B:
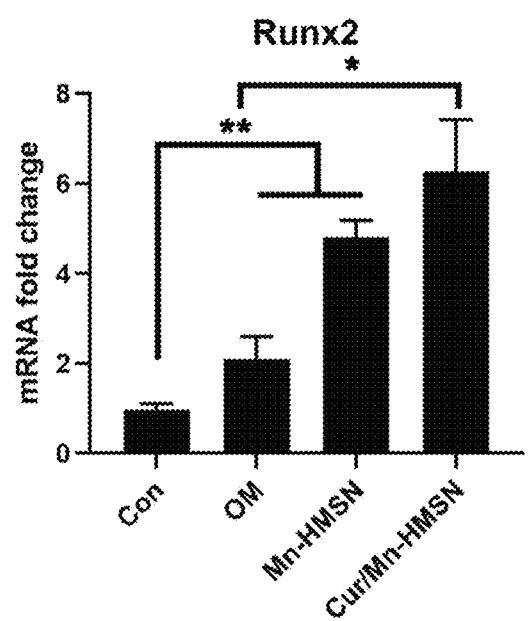
FIG. 9B shows the measurement results of Runx2 in Cur@Mn-HMSN group, Mn-HMSN group, Con group and OM group in the osteogenesis induction experiment, in which gray represents Con group, red represents OM group, blue represents Mn-HMSN group and green represents CUR @ Mn-HMSN.
Figure 9C:
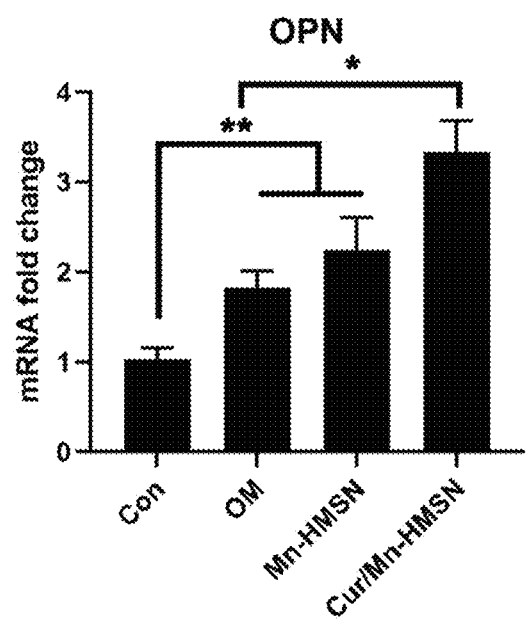
FIG. 9C shows the measurement results of OPN in Cur@Mn-HMSN group, Mn-HMSN group, Con group and OM group in the osteogenesis induction experiment, in which gray represents Con group, red represents OM group, blue represents Mn-HMSN group and green represents CUR @ Mn-HMSN.

The manganese-doped hollow mesoporous silica nanoparticles loaded with curcumin (Cur@Mn-HMSN) and PEG-modified manganese-doped silica particles (Mn-HMSN) prepared in Embodiment 1 are respectively added to DMEM substrate containing 10% fetal bovine serum, so that the concentration is 2.5 μg/mL, and the DMEM substrate containing 10% fetal bovine serum is used as blank control group (Con), and the osteogenic induction substrate is used as the reference group (OM).

hPDLSCs are inoculated in a 24-well plate, and the culture substrates prepared above are used for replacement respectively after the cells are attached to the wall. 7 days later, the substrates are decanted, rinsed twice with PBS, fixed with paraformaldehyde at a mass concentration of 4% for 10-15 min, rinsed twice with PBS, and alkaline phosphatase staining reagent (purchased from Beyotime Biotechnology) is added, and stained with the reagent under the protection of light for 15-30 min, and the results are shown in FIG. 7. As shown in FIG. 7, the experimental group containing Mn-HMSN shows a significant enhancement of cellular osteogenic differentiation as well as the strongest osteogenic effect in the Cur@Mn-HMSN group, suggesting that curcumin has a synergistic function with $Mn^{2+}$ in inducing osteogenesis.

hPDLSCs are inoculated in a 24-well plate, and the culture substrates prepared above are used for replacement respectively after the cells are attached to the wall. After 7 days, the substrates are decanted, rinsed twice with PBS, fixed with 4% paraformaldehyde for 10-15 min, rinsed twice with PBS, and the protein content is determined by the BCA assay and the intracellular alkaline phosphatase expression level is detected by using UV-absorbent assay. The results are shown in FIG. 8. The enhanced alkaline phosphatase activity of nanoparticle-treated periodontal ligament stem cells is evident as shown in FIG. 8.

hPDLSCs are inoculated in a 24-well plate, and the culture substrates prepared above are used for replacement respectively after the cells are attached to the wall. 7 days later, the substrates are decanted, rinsed twice with PBS, fixed with 4% paraformaldehyde for 10-15 min, rinsed twice with PBS, and RNA is extracted by a one-step method of guanidine isothiocyanate-phenol-chloroform, and changes in the level of transcripts of intracellular osteogenic marker genes are detected in the different treatment groups by qPCR method, with results as shown in FIG. 9A-FIG. 9C, where grey represents the Con group, red represents the OM group, blue represents the Mn-HMSN group, and green represents Cur@Mn-HMSN. From FIG. 9A-FIG. 9C, it is evident that after culturing the cells with the substrate containing Cur@Mn-HMSN for 7 days, the transcript levels of genes that represent the differentiation of the cells in the direction of osteogenicity, such as ALP, Runx2, and OPN, are increased to varying degrees, which implies that the prepared Cur@Mn-HMSN has a certain osteoinductive effect.

VI. In Vitro Anti-Inflammatory Detection

Figure 10A:
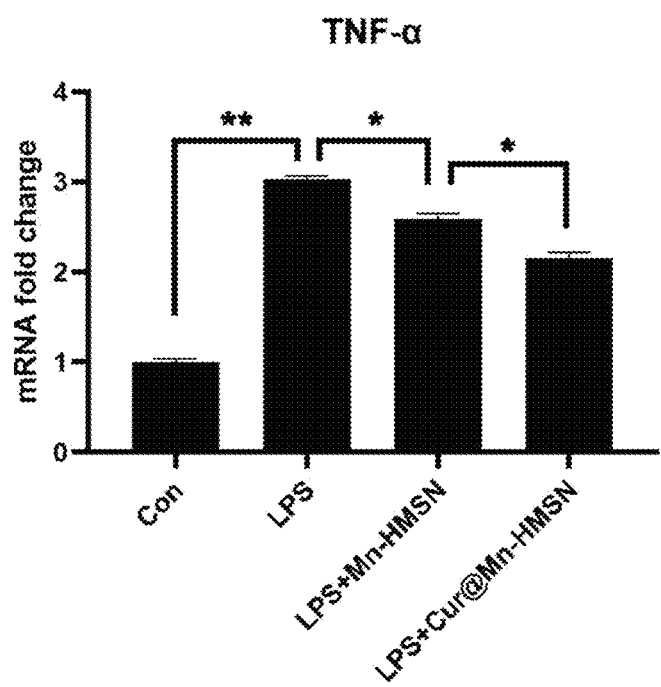
FIG. 10A is a graph showing the changes in the transcript levels of intracellular TNF-α in the Cur@Mn-HMSN group, the Mn-HMSN group, the LPS group and the Con group in the in vitro anti-inflammatory assay.
Figure 10B:
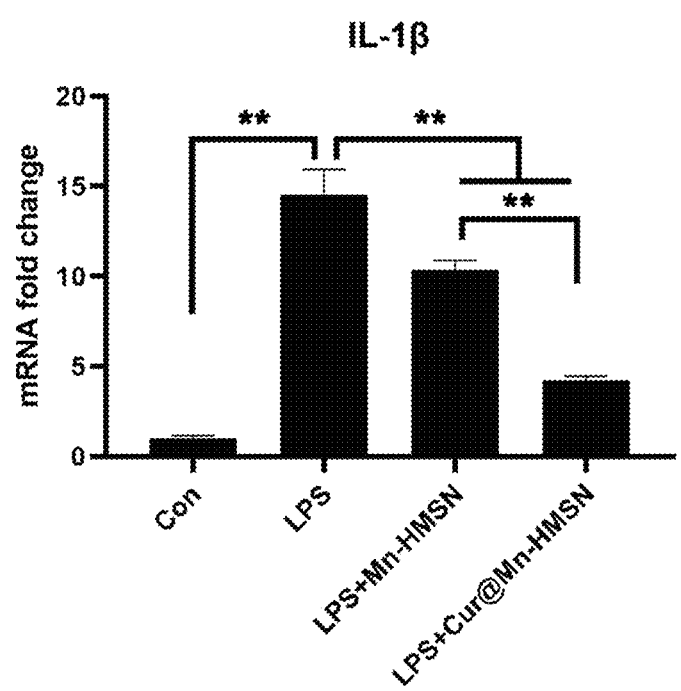
FIG. 10B is a graph showing the changes in the transcript levels of IL-1B in the Cur@Mn-HMSN group, the Mn- HMSN group, the LPS group and the Con group in the in vitro anti-inflammatory assay.
Figure 10C:
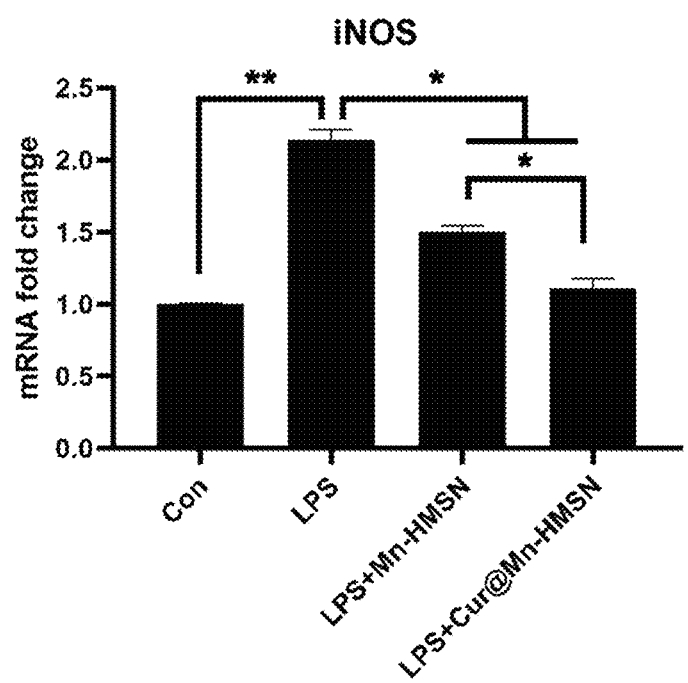
FIG. 10C is a graph showing the changes in the transcript levels of iNOS in the Cur@Mn-HMSN group, the Mn-HMSN group, the LPS group and the Con group in the in vitro anti-inflammatory assay.

Monocyte macrophage RAW264.7 is inoculated into a 6-well plate, and after wall attachment, LPS is added to the substrate to induce the M1 polarisation of the cells, 2.5 μg/mL of Cur@Mn-HMSN and Mn-HMSN (prepared as above) are added to the experimental group, and a blank control (Con) is set with no addition to the substrate, and the groups are continued to be cultured for 24 h. The cells are collected and RNA is extracted using guanidine thiocyanate-phenol-chloroform one-step method, and the changes in the transcript levels of the marker genes of intracellular macrophage M1 polarisation are detected by qPCR in different treatment groups. The results are shown in FIG. 10A-FIG. 10C, from which it is observed that the addition of the prepared Cur@Mn-HMSN nanoparticles significantly inhibits the LPS-induced changes in the transcriptional levels of TNF-α, IL-1B, and iNOS, suggesting that it has a better function of inhibiting the M1-directed polarisation of macrophages.

Figure 11:
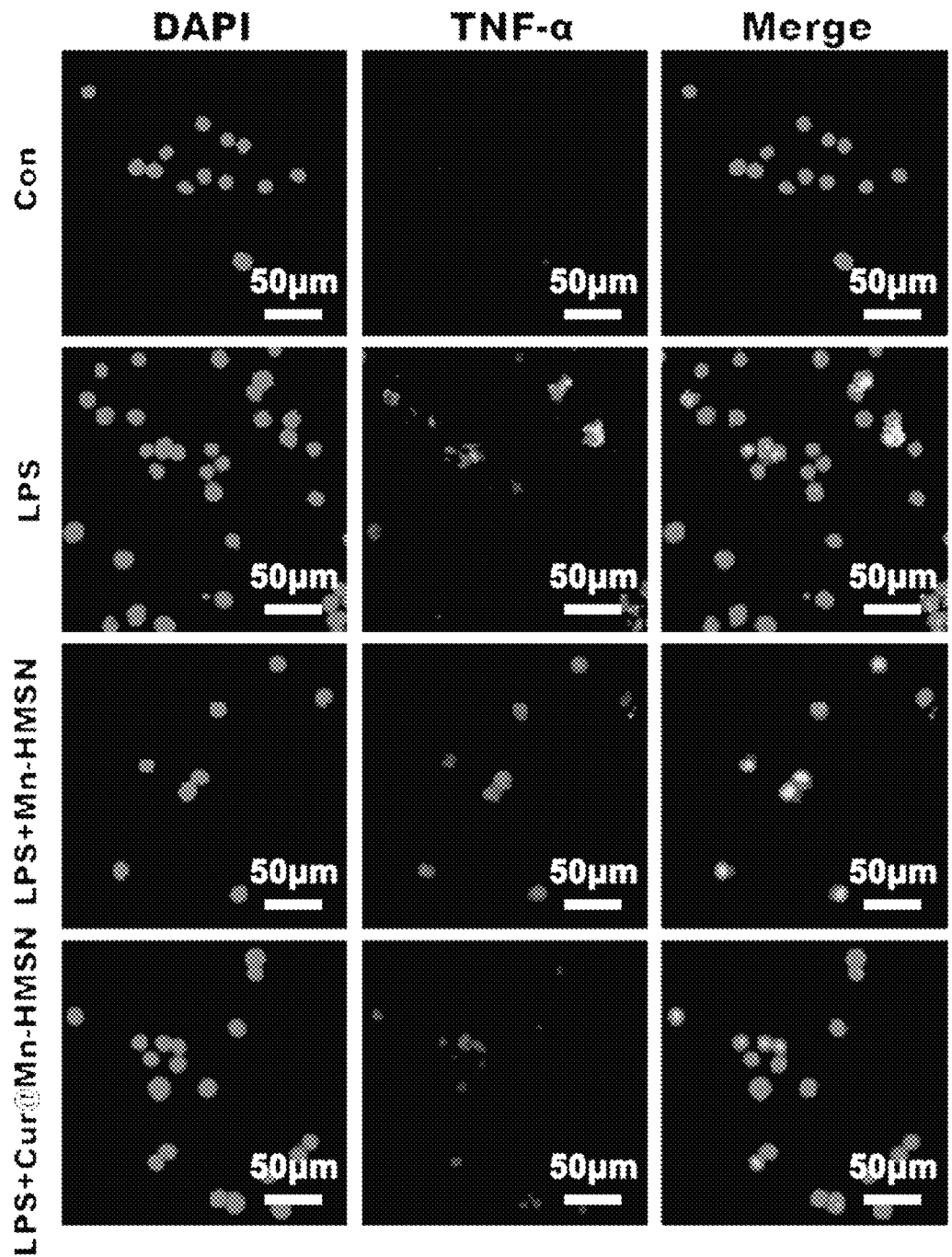
FIG. 11 shows the results of DAPI, TNF-α, and Merge confocal detection results in the Cur@Mn-HMSN, Mn-HMSN, LPS, and Con groups in the in vitro anti-inflammatory assay.

Monocyte macrophage RAW264.7 is inoculated into a 6-well plate, and after wall attachment, LPS is added to the substrate to induce the M1 polarisation, and 2.5 μg/mL of Cur@Mn-HMSN as well as Mn-HMSN (prepared as above) are added to the experimental group, and a blank control (Con) is set up by not adding anything to the substrate, and the groups are continued to be cultured for 24 h, respectively. Then, the supernatants are aspirated, rinsed twice with PBS, fixed with 4% paraformaldehyde for 10-15 min, rinsed twice with PBS, permeabilised with 1% TritonX-100 for 5 min at room temperature, rinsed three times with PBS, sealed with 5% BSA for 30 min, and then the primary antibody (TNF-α, 1:100) is added and placed overnight at 4° C., then rinsed three times with PBS, and the secondary antibody (1:200) is added and incubated at room temperature for 1 h, followed by rinsing by PBS for 3 times, DAPI staining for 5 min, rinsing for 3 times and confocal detection, the results are shown in FIG. 11, from which it is observed that the intracellular TNF-α expression level is significantly reduced in the group with the addition of Cur@Mn-HMSN.

Figure 12A:
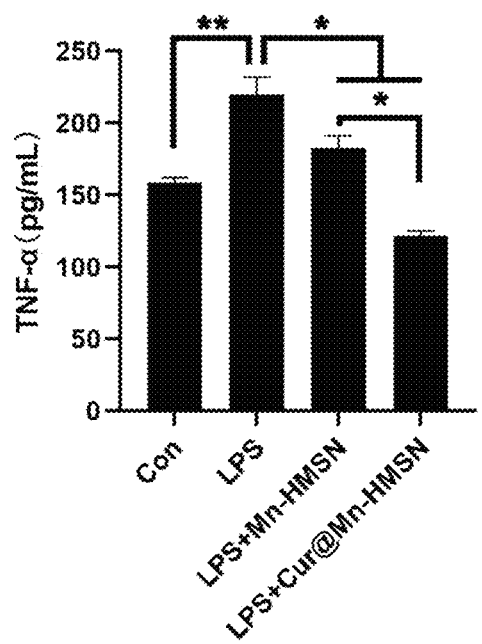
FIG. 12A shows the measurement results of IL-1ß contents in the supernatants of Cur@Mn-HMSN, Mn-HMSN, LPS, and Con groups in the in vitro anti-inflammatory assay.
Figure 12B:
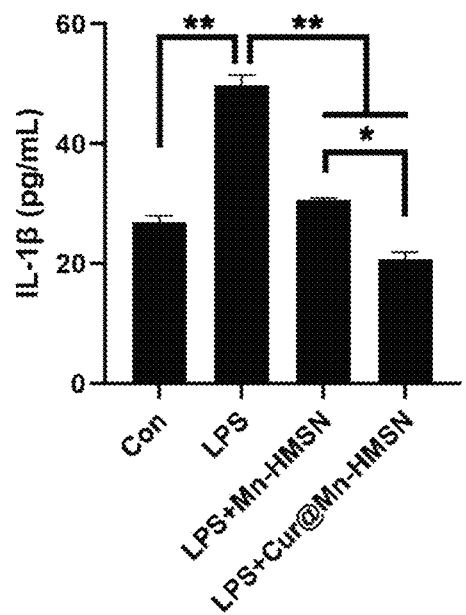
FIG. 12B shows the measurement results of TNF-α contents in the supernatants of Cur@Mn-HMSN, Mn-HMSN, LPS, and Con groups in the in vitro anti-inflammatory assay.
Figure 12C:
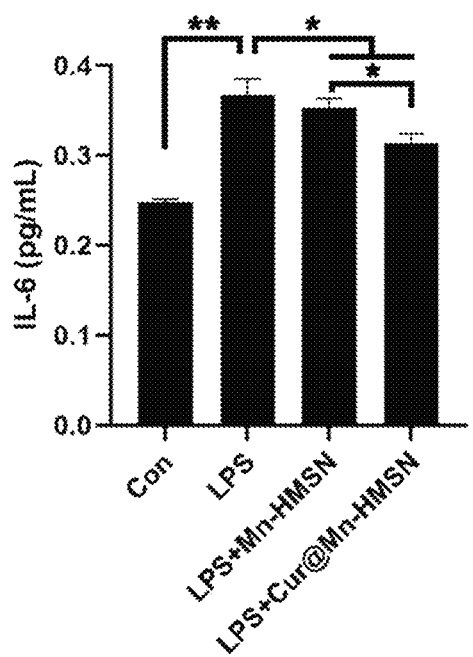
FIG. 12C shows the measurement results of IL-6 contents in the supernatants of Cur@Mn-HMSN, Mn-HMSN, LPS, and Con groups in the in vitro anti-inflammatory assay.

Monocyte macrophage RAW264.7 is inoculated into a 6-well plate, and after wall attachment, LPS is added to the substrate to induce the M1 polarisation, 2.5 μg/mL of Cur@Mn-HMSN and Mn-HMSN (prepared as above) are added to the experimental group, and a blank control (Con) is made by not adding anything to the substrate, and the groups are continued to be cultured for 24 h. The supernatants are aspirated, and the levels of IL-1β, TNF-α and IL-6 in the supernatants are detected by ELISA (using ELISA kit purchased from Shanghai Enzyme-linked Biotechnology Co., Ltd.). The results are illustrated in FIG. 12A-FIG. 12C, from which it is observed that the contents of IL-1β, TNF-α, and IL-6 in the group containing Cur@Mn-HMSN are 20.7±1.2 pg/mL, 121.3±3.8 pg/mL, and 0.31±0.01 pg/mL, respectively, which are significantly lower than that of the blank control group, and the above results demonstrate that the Cur@Mn-HMSN is capable of inhibiting LPS-induced macrophage polarisation and has a potential anti-inflammatory function.

VII. Detection of Bacteriostasis

Filter paper sheets with diameter of 5 mm are prepared by a hole punch, and after autoclaving, 20 μL of PBS, BP/Mn-HMSN (1 mg/mL) and Cur@BP/Mn-HMSN (1 mg/mL) are added dropwise onto the paper sheet, which may be used directly after evaporation of water on the surface of the paper sheet. Sterile filter paper sheets containing PBS, BP/Mn-HMSN and Cur@BP/Mn-HMSN are prepared.

Figure 13:
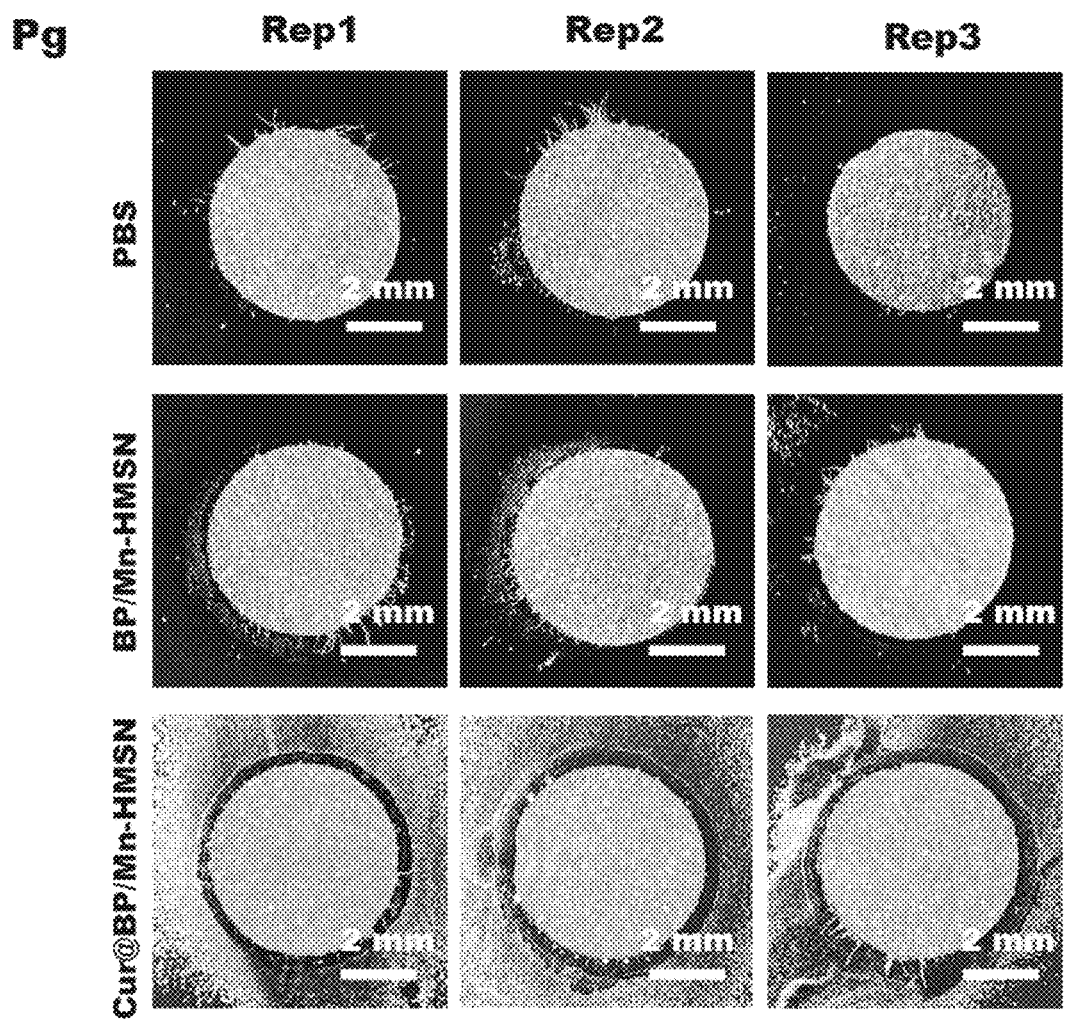
FIG. 13 shows the formation results of bacteriostatic circles in PBS, BP/Mn-HMSN and Cur@BP/Mn-HMSN groups in the antibacterial effect detection experiment.

The inhibition effect of nanoparticles on *Porphyromonas gingivalis* is detected by using the inhibition circle experiment, which is performed as follows: coating *Porphyromonas gingivalis* onto the agar medium of brain-heart extract, placing sterile filter paper sheets loaded with different nanoparticles on the surface of the petri dish, and incubating under anaerobic conditions at 37° C. for 2 days, and observing the formation of the inhibition circle around the filter paper. As shown in FIG. 13, a bacteriostatic circle is formed around the paper loaded with Cur@Mn-HMSN, suggesting a good bacteriostatic effect.

VIII. Verification Experiment of Mouse Periodontitis Model

The model of periodontitis in mice is established by silk thread ligation: the mice are injected intraperitoneally with 1% sodium pentobarbital (50 mg/kg) according to their body weight, and after complete anaesthesia, the mice are fixed on a mouse board in a supine position, and the mouth is opened using an opener; a 5-0 silk thread is placed at each end of the right maxillary second molar of mice with a needle holder, and the excess thread is cut after tying a knot on the buccal side, and the knot is tucked into the vestibular sulcus. The left maxilla serves as a healthy control group.

Figure 14:
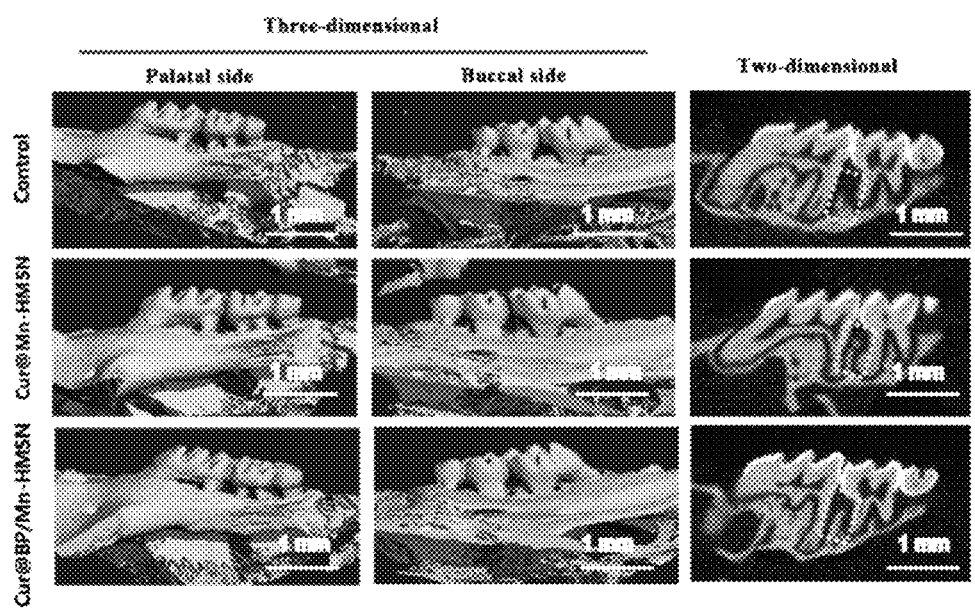
FIG. 14 shows the results of Micro-CT imaging scanning and histological staining analysis of PBS, BP/Mn-HMSN and Cur@BP/Mn-HMSN in the verification experiment of mouse periodontitis model.

The silk thread is removed 10 days after ligation, and 10 L of PBS, BP/Mn-HMSN, and Cur@BP/Mn-HMSN are injected into the subgingival periodontal tissues of the second maxillary molar on the right side of the periodontitis mice, respectively. Twenty-eight days after surgery, the maxillae of the mice are taken and fixed with 10% neutral formalin solution and then subjected to Micro-CT imaging scanning and histological staining analysis, the results are shown in FIG. 14, and the results of the determination of relative bone volume fraction (BV/TV), bone mineral density (BMD), and cementum-enamel junction to alveolar bone crest (CEJ-ABC) of each group are shown in FIG.

Figure 15A:
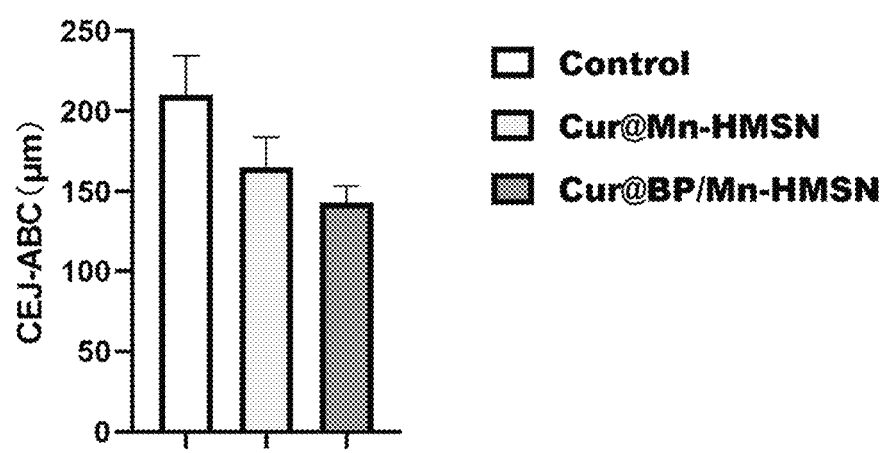
FIG. 15A shows the measurement results of cementum-enamel junction to alveolar bone crest (CEJ-ABC) of PBS, BP/Mn-HMSN and Cur@BP/Mn-HMSN in the validation experiment of mouse periodontitis model.
Figure 15B:
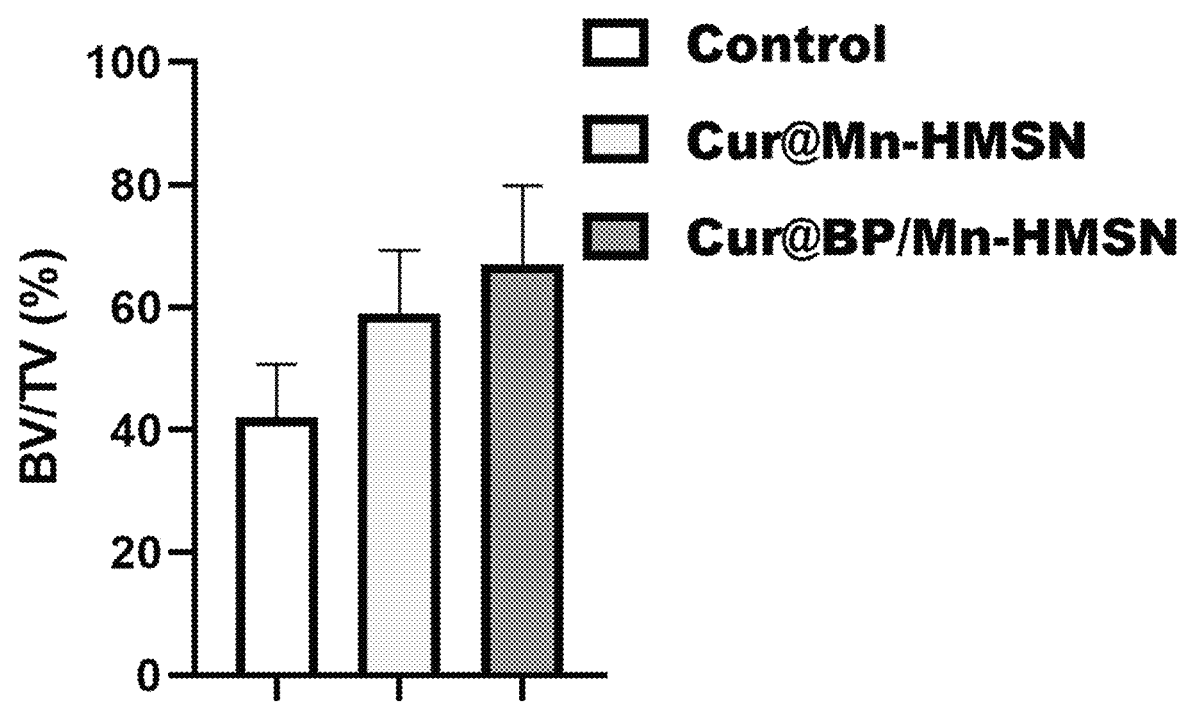
FIG. 15B shows the measurement results of relative bone volume fraction (BV/TV) of PBS, BP/Mn-HMSN and Cur@BP/Mn-HMSN in the validation experiment of mouse periodontitis model.
Figure 15C:
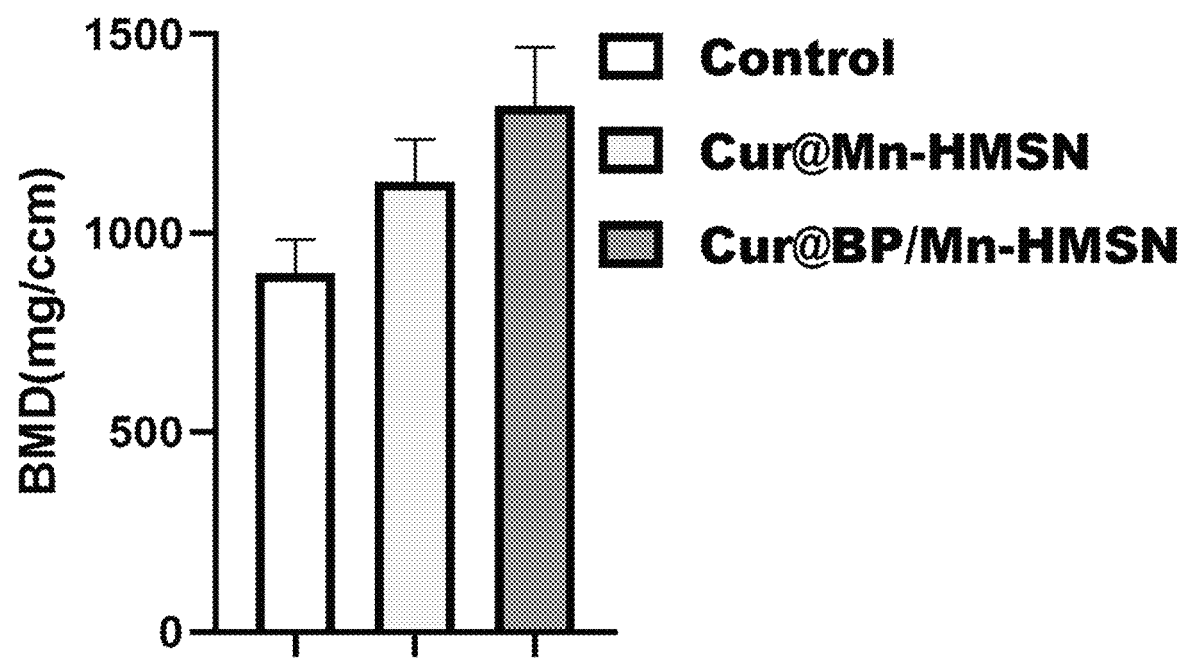
FIG. 15C shows the measurement results of bone mineral density (BMD) of PBS, BP/Mn-HMSN and Cur@BP/Mn-HMSN in the validation experiment of mouse periodontitis model.

15A-FIG. 15C; as may be observed in FIG. 15A-FIG. 15C, after periodontal injection of Cur@Mn-HMSN, the alveolar bone height of mice is significantly elevated, and the relative bone volume fraction (BV/TV) and bone mineral density (BMD) are increased, which is of statistical difference compared with the control group ($p<0.05$).

The above describes only the preferred embodiments of this application, but the protection scope of this application is not limited to this. Any change or replacement that may be easily thought of by a person familiar with this technical field within the technical scope disclosed in this application should be included in the protection scope of this application. Therefore, the protection scope of this application should be based on the protection scope of the claims.

What is claimed is:

1. A preparation method of manganese-doped hollow mesoporous silica nanoparticles loaded with curcumin, comprising the following steps:
    mixing silica nanoparticles with ethanol, ammonia, and cetyltrimethyl ammonium bromide to obtain a mixture aqueous solution, followed by dropwise adding 3-aminopropyltriethoxysilane to the mixture aqueous solution, and stirring and reacting for 2 h at room temperature, then continuing stirring for 24 h at 50° C., followed by centrifugation to obtain mesoporous silica particles with a shell-core structure;
    mixing the mesoporous silica particles with the shell-core structure with a sodium carbonate solution for reaction, obtaining aminated silica particles with hollow structure;
    mixing and stirring the aminated silica particles with hollow structure with manganese chloride, dropwise adding ammonia water for a hydrothermal reaction, and washing to obtain manganese-doped hollow mesoporous silica nanoparticles;
    dispersing the manganese-doped hollow mesoporous silica nanoparticles in a borate buffer salt solution, then adding active ester-polyethylene glycol-carboxyl group for overnight reaction to obtain PEG-modified manganese-doped silica particles;
    dispersing the PEG-modified manganese-doped silica particles with borate buffer salt solution, adding ethyl dimethylaminopropyl carbodiimide and N-hydroxysuccinimide for reaction, then adding alendronate for reaction, and obtaining biphosphonate-modified silica particles; and
    adding the bisphosphonate-modified silica particles into a curcumin solution for reaction, centrifuging and rinsing to obtain the manganese-doped hollow mesoporous silica nanoparticles loaded with curcumin.

2. The preparation method of the manganese-doped hollow mesoporous silica nanoparticles loaded with curcumin according to claim 1, wherein a material-liquid ratio of the silica nanoparticles to 3-aminopropyltriethoxysilane and cetyltrimethyl ammonium bromide is 10-50 mg:20 μL:11.2 mg.

3. The preparation method of the manganese-doped hollow mesoporous silica nanoparticles loaded with curcumin according to claim 1, wherein a concentration of the sodium carbonate solution is 1 M, and an addition of the sodium carbonate solution is followed by stirring and reacting at 45° C. for 6 h.

4. The preparation method of the manganese-doped hollow mesoporous silica nanoparticles loaded with curcumin according to claim 1, wherein a dosage ratio of the manganese-doped hollow mesoporous silica nanoparticles to the active ester-polyethylene glycol-carboxyl group is 10-50 mg:100 mg.

5. The preparation method of the manganese-doped hollow mesoporous silica nanoparticles loaded with curcumin according to claim 1, wherein a dosage ratio of the aminated silica particles with hollow structure to the manganese chloride is 10-50 mg:20 mg.

6. The preparation method of the manganese-doped hollow mesoporous silica nanoparticles loaded with curcumin according to claim 1, wherein a dosage ratio of the PEG-modified manganese-doped silica particles to the ethyl dimethylaminopropyl carbodiimide, N-hydroxysuccinimide and alendronate is 10-50 mg:12 mg:8 mg:8 mg, and the alendronate is added to react overnight at room temperature.

7. The preparation method of the manganese-doped hollow mesoporous silica nanoparticles loaded with curcumin according to claim 1, wherein a mass ratio of the bisphosphonate-modified silica particles to curcumin in the curcumin solution is 1:1, and the bisphosphonate-modified silica particles are added into the curcumin solution and reacted by shaking overnight away from light.

* * * * *